United States Patent [19]

Harnisch

[11] 4,152,330
[45] May 1, 1979

[54] PROCESS FOR THE PREPARATION OF NAPHTHOSTYRIL

[75] Inventor: Horst Harnisch, Much, Germany

[73] Assignee: Bayer Aktiengesellschaft, Leverkusen, Fed. Rep. of Germany

[21] Appl. No.: 822,247

[22] Filed: Aug. 5, 1977

[30] Foreign Application Priority Data

Aug. 7, 1976 [DE] Fed. Rep. of Germany ....... 2635693
Jan. 8, 1977 [DE] Fed. Rep. of Germany ....... 2700649

[51] Int. Cl.² .......................................... C07D 209/92
[52] U.S. Cl. ............................................. 260/326.5 B
[58] Field of Search ................................. 260/326.5 B

[56] References Cited

U.S. PATENT DOCUMENTS 2,628,964   2/1953   Scalera .......................... 260/326.5 B

OTHER PUBLICATIONS

Dokunikhin, C.A. 55, 21139i (1959).

Primary Examiner—Mark L. Berch
Attorney, Agent, or Firm—Plumley and Tyner

[57] ABSTRACT

Naphthostyril is obtained in high space/time yields by reacting 1-naphthyl isocyanate with an anhydrous aluminium halide in an inert solvent, carrying out the reaction in a homogeneous solution using 700–1.800 ml of solvent per mol of 1-naphthyl isocyanate in the temperature range from 140–160° C. and — after hydrolysis of the reaction mixture — separating the phases. Naphthostyril is an intermediate for preparation of dyestuffs.

8 Claims, No Drawings

PROCESS FOR THE PREPARATION OF NAPHTHOSTYRIL

Naphthostyril is a known intermediate product for valuable dyestuffs. Furthermore, it is known from U.S. Pat. No. 2,628,964 that naphthostyril can be prepared by the following route: reaction of 1-naphthyl isocyanate with $AlCl_3$ in o-dichlorobenzene or trichlorobenzene at 100°–200° C., with intramolecular Friedel-Crafts acylation of the free periposition of the naphthalene, subsequent hydrolysis of the $AlCl_3$ complex using dilute hydrochloric acid, removal of the organic solvent, intermediate isolation of the crude naphthostyril, purification via the stage of forming a solution of the alkali metal salt of 1-aminonaphthalene-8-carboxylic acid, acid recyclisation to the lactam and isolation of the naphthostyril by filtering off.

However, the process has some serious disadvantages. In order to avoid competing intermolecular Friedel-Crafts acylations and resinifications, the process had to be carried out in a high dilution (the weight ratio indicated in the examples of 1-naphthyl isocyanate to o-dichlorobenzene is about 1:20). The space/time yield is thus low and relatively high costs are incurred by distilling off large amounts of solvent with steam.

The object was to improve the process so that it is economical.

It has now been found, surprisingly, that when the procedure is carried out with considerably higher concentrations the side reactions, which reduce the yield, can be avoided and very pure naphthostyril can be obtained in high yield if the aluminium halide is not reacted, as recommended hitherto, in a suspension with the 1-naphthyl isocyanate, but is first completely dissolved in an aromatic halogenohydrocarbon, by warming, and the solution of 1-naphthyl isocyanate in an inert solvent is added to this solution.

In addition to aluminium chloride, aluminium bromide can also be used as the aluminium halide. Examples of suitable aromatic halogenohydrocarbons are chlorobenzene, bromobenzene, chlorotoluenes, dichlorobenzenes, dichlorotoluenes and trichlorobenzenes. 1,2,4-Trichlorobenzene, dichlorotoluenes (mixture of isomers) and, in particular, o-dichlorobenzene or a mixture of isomeric dichlorobenzenes are particularly preferred.

In addition to the aromatic halogenohydrocarbons mentioned above, aromatic hydrocarbons, such as toluene or xylene, or non-aromatic halogenohydrocarbons, such as perchloroethylene, can also be used as inert solvents for 1-naphthyl isocyanate. Preferably, the same solvent is used as for dissolving the aluminium halide.

Under "inert solvents" are to be understood those solvents which remain essentially unchanged under the reaction conditions.

In order to dissolve the aluminium halide in the aromatic halogenohydrocarbon, the suspension is appropriately warmed to about 130°–180° C., preferably 145°–165° C., at least until the aluminium halide has gone completely into solution.

Occasionally, small amounts of aluminium salt precipitate as a colourless sublimate on cooler parts of the reaction vessel when the aluminium halide is dissolved in the aromatic halogenohydrocarbon. This does not interfere with the subsequent course of the reaction if it is ensured that the 1-naphthyl isocyanate solution runs directly into the clear solution. It is essential only that the solution itself is free from undissolved portions of aluminium halide.

Further preferred reaction conditions are:

a. The use of not less than 1.5, preferably 1.9–2.5, equivalents of aluminium halide;

b. A reaction temperature range from 140°–160° C., in particular 144°–156° C.;

c. The use, per mol of 1-naphthyl isocyanate, of at least 350 ml of the aromatic halogenohydrocarbon for dissolving the aluminium halide and of at least 300 ml of the inert solvent for diluting the 1-naphthyl isocyanate (a total volume of the solvents used in the reaction of 700–1,800 ml, in particular 800–1,500 ml).

In the case where o-dichlorobenzene is used as the solvent, the preferred embodiment of the process is characterised in that 1-naphthyl isocyanate is dissolved in at least the 2.3-fold amount by weight of o-dichlorobenzene, this solution is run into a solution of 1.9–2.5 mols of anhydrous aluminium halide in at least the 2.7-fold amount by weight, relative to 1-naphthyl isocyanate, of o-dichlorobenzene at 144° to 156° C., the mixture is cooled and/or worked up by hydrolysis, with the proviso that the total amount of solvent used in the reaction is 5.7–11.6 times the amount of 1-naphthyl isocyanate employed. The hydrolysis can be carried out in the customary manner with water or, preferably, with dilute hydrochloric acid. The hydrolysis temperature can be varied within a wide range, for example between 0° and 150° C. After the hydrolysis of the aluminium halide complex, naphthostyril crystallises out of the organic phase on cooling, in the presence of the aqueous phase. If the reaction is carried out in the high concentration range, say with a total volume of organic solvent of 700–1,300 ml per mol of 1-naphthyl isocyanate, the naphthostyril crystallises out virtually completely after the hydrolysis and can be isolated, almost without loss, directly by filtering off (filtering off by suction, squeezing out, centrifuging or the like) without previous distillation. The further purification can then be carried out in a known manner by dissolving in warm alkali metal hydroxide solution, clarifying by filtration, acidifying, warming, cooling and filtering off. Redissolving in about 1.9–3 equivalents of alkali metal hydroxide solution and reprecipitation is preferred.

An advantageous working-up process which gives very pure naphthostyril without intermediate isolation of the crude product consists in initially, after the hydrolysis of the reaction solution, separating off the organic phase hot from the aqueous phase containing the aluminium salts, extracting the naphthostyril from the organic phase with warm dilute alkali metal hydroxide solution, separating off the aqueous-alkaline extract from the organic phase, warming this extract, after clarifying by filtration, with aqueous mineral acid and then isolating the crystalline precipitate in the customary manner.

In general, the naphthostyril has the required solubility in the inert hot organic solvent. Only in the high concentration range, say a total volume of organic solvent between 700 and 850 ml, may a slight subsequent dilution of the solvent be necessary.

Advantageously, the phase separation after the hydrolysis is carried out at temperatures of at least 70° C. (in particular 80°–110° C.), the subsequent extraction with alkali metal hydroxide solution is carried out at at least 40° C. (for example 50°–150° C.), the clarifying by filtration is carried out at room temperature or at elevated temperature (for example 30°–150° C.) and the acid treatment is carried out at at least 30° C. (preferably at 60°–110° C.). The addition of commercially available clarifying or filtration auxiliaries, such as cellulose powder, Tonsil, active charcoal and/or kieselguhr during the alkaline clarification by filtration has proved effective. Preferred alkali metal hydroxide solutions are sodium hydroxide solution and potassium hydroxide solution and preferred mineral acids are sulphuric acid and hydrochloric acid.

For a complete extraction of the naphthosytril from the organic phase, relatively small volumes of dilute alkali metal hydroxide solution are already sufficient, that is to say 650 ml per mol, with a content of the order of magnitude of 2–5 mols of alkali metal hydroxide. Larger volumes, for example, 2 liters of alkali metal hydroxide solution, give naphthostyril of the same quality and yield.

Since 1-amino-naphthalene-8-carboxylic acid (alkali metal salt) has proved to be sensitive to air, the alkaline extraction of naphthostyril and further processing up to acidification is advantageously carried out in an inert gas atmosphere (preferably nitrogen). Likewise, it has proved effective to add small amounts of sodium dithionite, for example 1–10 g per mol of naphthostyril, for protection against autoxidation in the alkaline medium. The amount of mineral acid is so chosen that it is sufficient at least for neutralisation. The mixture is advantageously rendered strongly acid (pH $\leq$ 2). The isolation of the crystalline naphthostyril from the aqueous suspension can be carried out with the aid of known filtration methods. The residue is then washed with water until free from salts and the product is appropriately dried at 70°–100° C. in vacuo.

A particularly simple, advantageous working-up process in which both the intermediate isolation of the crude product and the alkaline purification are omitted consists in initially, after the hydrolysis of the reaction solution, separating off the organic phase hot, as described above, from the aqueous phase containing the aluminium salts, then clarifying the organic phase through a filter which is resistant to acid, if appropriate with the addition of a clarifying and/or filtration auxiliary, if appropriate concentrating the filtrate and cooling and isolating the crystalline precipitate. The naphthostyril, which is obtained in very good yield, has a high degree of purity (about 99%).

EXAMPLE 1

292.6 g (2.2 mols) of anhydrous aluminium chloride are introduced into 700 ml (910 g) of anhydrous o-dichlorobenzene, the suspension is warmed to 160° C. for 30 minutes, whilst stirring slowly, and allowed to cool to 150° C., whilst stirring, and a solution of 169 g (1 mol) of 1-naphthyl isocyanate in 460 ml (600 g) of anhydrous o-dichlorobenzene is allowed to run in at 148°–153° C. in the course of 30 minutes. The solution is then cooled to 80° C. and discharged into a mixture of 560 ml of water and 300 g of 37% strength hydrochloric acid, the reaction vessel is rinsed out with 200 ml of o-dichlorobenzene, the mixture is stirred for 45 minutes at 95° C. and allowed to settle for about 10 minutes, the main proportion of the organic upper phase is siphoned off, 50 ml of isopropanol are added to the residual phase mixture, the mixture is stirred briefly and allowed to settle again and the main proportion of the aqueous lower phase is separated off, still at 95° C. The remaining two-phase mixture is washed with 500 ml of hot water and the organic phase is allowed to settle at the bottom and is separated off.

800 ml of water are added to the combined organic phases, the pH of the mixture is adjusted to 10 with sodium hydroxide solution, 168 g (2 mols) of 45% strength sodium hydroxide solution are added, under nitrogen, and the mixture is warmed to 95° C. for 1 hour. The mixture is allowed to settle for about 1 hour, the organic lower phase is substantially separated off, the remaining suspension is stirred with 5 g of kieselguhr and 5 g of cellulose powder and filtered, still under $N_2$, the residue on the filter is rinsed with 100 ml of water, the residual organic lower phase is completely drained off from the filtrate, the alkaline-aqueous solution is warmed to 95° C. again with 4 g of sodium dithionite and allowed to run into 600 g of 18% strength hydrochloric acid, heated to 90° C., the mixture is subsequently stirred for 30 minutes at 90°–95° C. and cooled to 50° C. and the crystalline precipitate is filtered off, washed with water until free from salts and dried at 80° C. in vacuo.

Yield: 135 g = 80% of theory.
Purity: 99%.

If a mixture of isomeric dichlorobenzenes (80% of o-dichlorobenzene, 15% of m-dichlorobenzene and 5% of p-dichlorobenzene) is employed instead of o-dichlorobenzene, the same result is obtained.

The examples listed in the table which follows show the yields which are obtained when individual parameters are changed, using an otherwise identical procedure. In each case the purity of the products is over 99%.

| Ex. | | Yield | (of theory) |
|---|---|---|---|
| 2 | Reaction temperature: 140°–145° C. | 129 g | (76%) |
| 3 | 155°–160° C. | 128 g | (76%) |
| 4 | 144°–156° C. | 135 g | (80%) |
| 5 | Period over which the 1-naphthyl isocyanate solution is added: | | |
| | 45 minutes | 132 g | (78%) |
| 6 | 60 minutes | 126 g | (75%) |
| 7 | 80 minutes | 128 g | (76%) |
| 8 | Subsequent reaction at 148°–153° C. | | |
| | 10 minutes | 129 g | (76%) |
| 9 | 20 minutes | 128 g | (76%) |
| 10 | 30 minutes | 115 g | (68%) |
| 11 | Extraction with NaOH: 252 g of 45% strength (3 mols) and 1,000 ml of water (acidified with 900 g of 18% strength HCl) | 135 g | (80%) |
| 12 | Extraction with NaOH: 336 g of 45% strength (4 mols) and 1,200 ml of water (acidified with 1,200 g of 18% strength HCl) | 135 g | (80%) |
| 13 | Extraction with NaOH: 420 g of 45% strength (5 mols) and 1,400 ml of water (acidified with 1,500 g of 18% strength HCl) | 135 g | (80%) |
| 14 | Extraction with NaOH; 80 g (2 mols) / 600 ml $H_2O$ | 135 g | (80%) |
| 15 | Extraction with KOH: 112 g (2 mols) / 1,000 ml $H_2O$ | 135 g | (80%) |
| 16 | Extraction with NaOH: | | |
| | 15 hours, 40° C. | 135 g | (80%) |
| 17 | 12 hours 50° C. | 135 g | (80%) |
| 18 | 6 hours, 60° C. | 135 g | (80%) |
| 19 | 1.5 hours, 80° C. | 135 g | (80%) |
| 20 | 1 hour 110° C. | 135 g | (80%) |
| 21 | HCl treatment after the extraction, pH $\leq$ 2 | | |
| | 24 hours, 25° C. | 135 g | (80%) |
| 22 | 12 hours, 30° C. | 135 g | (80%) |
| 23 | 4.5 hours, 40° C. | 135 g | (80%) |
| 24 | 1.5 hours, 50° C. | 135 g | (80%) |
| 25 | 0.5 hours, 60° C. | 135 g | (80%) |

-continued

| Ex. | | Yield | (of theory) |
|---|---|---|---|
| 26 | 15 minutes, 80° C. | 135 g | (80%) |
| 27 | 5 minutes, 100° C. | 135 g | (80%) |
| 28 | 3 minutes, 110° C. | 135 g | (80%) |
| 29 | 30 hours, 60° C. 9(pH = 6) | 135 g | (80%) |
| 30 | 20 hours, 80° C. | 135 g | (80%) |
| 31 | 1 hour, 100° C. | 135 g | (80%) |
| 32 | 600 g of 24% strength sulphuric acid instead of 18% strength HCl | 135 g | (80%) |
| 33 | without the addition of isopropanol | 133 g | (79%) |
| 34 | n-propanol instead of isopropanol | 135 g | (80%) |
| 35 | 2-methoxyethanol instead of isopropanol | 135 g | (80%) |
| 36 | 2-ethoxyethanol instead of isopropanol | 135 g | (80%) |
| 37 | equivalent amount of $AlBr_3$ instead of $AlCl_3$ | 135 g | (80%) |
| 38 | amount of o-dichlorobenzene used in the reaction: 900 ml (for $AlCl_3$) + 600 ml (for isocyanate) | 135 g | (80%) |

EXAMPLE 39

169 g of naphthyl isocyanate are reacted with 292.6 g of $AlCl_3$ in the manner indicated in Example 1 and the mixture is worked up as follows:

The reaction solution, heated to 80° C., is discharged into a mixture of 560 ml of water and 20 g of 37% strength hydrochloric acid, the reaction vessel is rinsed out with 200 ml of o-dichlorobenzene, the mixture is heated to the boil for 5 hours, 640 ml of water are added, the mixture is heated to the boil for a further hour and allowed to settle for about 5 minutes, the organic lower phase is separated off at 95°–100° C., 800 ml of water are added to the organic phase and the mixture is further processed exactly as indicated in Example 1.

Yield: 135.5 g (80% of theory)
Purity: 99.5%

The same result is obtained if the phase separation is carried out at 70°–80° C.

The same result is also obtained if the hydrolysis is carried out from the beginning with 1,200 ml of water and 20 g of 37% strength HCl (heat to the boil for 5 hours).

EXAMPLE 40

292.6 g (2.2 mols) of anhydrous $AlCl_3$ are introduced into 500 ml (650 g) of anhydrous o-dichlorobenzene, the suspension is warmed to 160° C., whilst stirring slowly, until the $AlCl_3$ is dissolved and allowed to cool to 150° C., whilst stirring, and a solution of 169 g (1 mol) of 1-naphthyl isocyanate in 420 ml (540 g) of anhydrous o-dichlorobenzene is allowed to run in at 148°–153° C. in the course of 30 minutes. The mixture is then cooled to 80° C., the solution is discharged into a mixture of 3,000 g of ice water and 300 g of 37% strength HCl so that the temperature is kept below 30° C., the resulting mixture is stirred for 2 hours at temperatures of below 30° C. and the crystalline precipitate is filtered off, washed with 5 liters of water and dried at 90° C. in vacuo.

Yield: 135.7 g of naphthostyril (= 80% of theory)
Purity: 96%

The same result is obtained if chlorobenzene or chlorotoluene is employed instead of o-dichlorobenzene and the reaction is carried out in a closed reaction vessel.

If instead of 292.6 g (2.2 mols), 333 g (2.5 mols) of $AlCl_3$ in 570 ml of o-dichlorobenzene are employed, 134 g (79% of theory) of naphthostyril are obtained with a purity of 96%.

If 240 g (1.8 mols) of $AlCl_3$ in 350 ml of o-dichlorobenzene are used and a solution of 169 g of 1-naphthyl isocyanate in 350 ml of o-dichlorobenzene is allowed to run in, 108 g (64% of theory) of naphthostyril are obtained with a purity of 94%. The same result (108 g) is obtained if only 300 ml of o-dichlorobenzene are used to dissolve the naphthyl isocyanate and 400 ml are used to dissolve the $AlCl_3$.

EXAMPLE 41

169 g of naphthyl isocyanate are reacted with 292.6 g of $AlCl_3$ in the manner indicated in Example 1 and the mixture is worked up as follows:

The reaction solution, heated to 80° C., is discharged into a mixture of 1,200 ml of water and 20 g of 37% strength HCl, the reaction vessel is rinsed out with 200 ml of o-dichlorobenzene, the mixture is heated to the boil for 6 hours and allowed to settle for about 5 minutes, the organic lower phase is separated off and 10 g of Tonsil and 30 g of cellulose powder are added to this, the solvent, containing water, is distilled off at 90°–95° C. (40–50 mm Hg) until the distillate passing over is clear, the solution is filtered through a filter which is resistant to acid, the residue is washed with 50 ml of hot o-dichlorobenzene, the combined filtrates are evaporated to half their volume at 90°–95° C. (40–50 mm Hg) and cooled to 20° C., whilst stirring, and the crystalline precipitate is filtered off, washed with a little cold toluene and dried at 85° C. in vacuo.

Yield: 132 g of naphthostyril (= 78% of theory); purity: 99.1%.

The same result is obtained if equal volumes of 1,2,4-trichlorobenzene or dichlorotoluene (mixture of isomers) are employed instead of o-dichlorobenzene, or if the hydrolysis is carried out for 3 hours at 150° C. in a closed reaction vessel.

I claim:

1. Process for the preparation of naphthostyril by reacting 1-naphthyl isocyanate with an anhydrous aluminium halide in an inert solvent, characterised in that the reaction is carried out in a homogeneous solution using 700–1,800 ml of solvent per mol of 1-naphthyl isocyanate in the temperature range from 140°–160° C.

2. Process according to claim 1, characterised in that the reaction is carried out using 800–1,500 ml of solvent per mol of 1-naphthyl isocyanate in a homogeneous solution in the temperature range from 144°–156° C.

3. Process according to claim 1, characterised in that, per mol of 1-naphthyl isocyanate, 1.9–2.5 mols of aluminium halide are completely dissolved in at least 350 ml of an aromatic halogenohydrocarbon, with warming, a solution of 1-naphthyl isocyanate in at least 300 ml of an inert solvent from the aromatic or non-aromatic halogenohydrocarbon or aromatic hydrocarbon series is added in the temperature range from 144°–156° C. and is then cooled and/or worked up by hydrolysis, with the proviso that the total volume of solvent used for the reaction is 700–1,800 ml.

4. Process according to claim 1, characterised in that aluminium chloride or aluminium bromide is employed as the aluminium halide and an aromatic hydrocarbon from the series of chlorobenzenes, chlorotoluenes, dichlorobenzenes, dichlorotoluenes, trichlorobenzenes and/or bromobenzene is employed as the inert solvent.

5. Process according to claim 1, characterised in that o-dichlorobenzene or a mixture of isomeric dichlorobenzenes is employed as the inert solvent.

6. Process according to claim 1, characterised in that the reaction solution is further worked up after the hydrolysis by separating the organic phase from the aqueous phase containing the aluminium salts at temperatures of at least 70° C.

7. Process according to claim 1, characterised in that after the hydrolysis of the reaction solution the organic phase is initially separated off from the aqueous phase containing the aluminium salts at temperatures of at least 70° C., the naphthostyril is extracted, as the alkali metal salt of 1-aminonaphthalene-8-carboxylic acid, from the organic phase with dilute alkali metal hydroxide solution at at least 40° C. and, if desired, is further worked up in a known manner.

8. Process according to claim 1, characterised in that after the hydrolysis of the reaction solution the organic phase is initially separated off from the aqueous phase containing the the aluminium salts at temperatures of at least 70° C. and is clarified through a filter which is resistant to acid, the filtrate is concentrated and cooled and the crystalline precipitate is isolated.

* * * * *